US00PP30851P2

(12) United States Plant Patent
Fear et al.

(10) Patent No.: US PP30,851 P2
(45) Date of Patent: Aug. 27, 2019

(54) STRAWBERRY PLANT VARIETY NAMED 'DRISSTRAWFIFTYEIGHT'

(50) Latin Name: *Fragaria x ananassa*
Varietal Denomination: DrisStrawFiftyEight

(71) Applicant: Driscoll's, Inc., Watsonville, CA (US)

(72) Inventors: Carlos D. Fear, Aptos, CA (US); Katalin Monika Pakozdi, Maidstone (GB); Alessandra Lillo, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 15/998,014

(22) Filed: Jun. 11, 2018

(51) Int. Cl.
*A01H 5/08* (2018.01)
*A01H 6/74* (2018.01)

(52) U.S. Cl.
USPC ..... Plt./209
CPC ..... *A01H 6/74* (2018.05); *A01H 5/08* (2013.01)

(58) Field of Classification Search
USPC ..... Plt./208, 209
CPC ..... A01H 5/0893
See application file for complete search history.

(56) References Cited

U.S. PATENT DOCUMENTS

PP1,745 P 8/1958 Lang
PP3,981 P 11/1976 Bringhurst et al.
PP4,487 P 11/1979 Bringhurst et al.
PP4,538 P 5/1980 Bringhurst et al.
PP5,262 P 7/1984 Voth et al.
PP5,265 P 7/1984 Voth et al.
PP5,266 P 7/1984 Bringhurst et al.
PP5,300 P 10/1984 Johnson, Jr.
PP5,480 P 5/1985 Nakagawa
PP5,840 P 12/1986 Johnson, Jr. et al.
PP6,191 P 5/1988 Johnson, Jr. et al.
PP6,231 P 7/1988 Johnson, Jr. et al.
PP6,578 P 1/1989 Voth et al.
PP6,579 P 1/1989 Bringhurst et al.
PP7,024 P 9/1989 Johnson, Jr. et al.
PP7,172 P 2/1990 Voth et al.
PP7,522 P 5/1991 Johnson, Jr. et al.
PP7,614 P 8/1991 Bringhurst et al.
PP7,615 P 8/1991 Bringhurst et al.
PP8,086 P 1/1993 Nelson et al.
PP8,205 P 4/1993 Nelson et al.
PP8,649 P 3/1994 Sjulin et al.
PP8,661 P 3/1994 Bringhurst et al.
PP8,708 P 5/1994 Voth et al.
PP8,745 P 5/1994 Sjulin et al.
PP9,130 P 5/1995 Sjulin et al.
PP9,909 P 6/1997 Ackerman et al.
PP10,221 P 2/1998 Sjulin et al.
PP10,534 P 8/1998 Sjulin et al.
PP10,642 P 10/1998 Amorao et al.
PP11,035 P 8/1999 Mowrey et al.
PP11,277 P 3/2000 Gilford et al.
PP11,279 P 3/2000 Gilford et al.
PP11,522 P 9/2000 Amorao et al.
PP11,548 P 10/2000 Amorao et al.
PP11,554 P 10/2000 Sjulin et al.
PP11,639 P 11/2000 Mowrey et al.
PP12,186 P2 11/2001 Gilford et al.
PP12,436 P2 3/2002 Amorao et al.
PP12,577 P2 4/2002 Amorao et al.
PP12,817 P2 7/2002 Gilford et al.
PP12,889 P2 8/2002 Lamb et al.
PP12,899 P2 9/2002 Mowrey et al.
PP13,386 P2 12/2002 Mowrey et al.
PP13,469 P3 1/2003 Larson et al.
PP14,005 P3 7/2003 Amorao et al.
PP14,062 P3 8/2003 Amorao et al.
PP14,109 P3 8/2003 Gilford et al.
PP14,771 P3 5/2004 Amorao et al.
PP15,145 P2 9/2004 Mowrey et al.
PP15,308 P2 11/2004 Sjulin et al.
PP15,375 P2 11/2004 Mowrey et al.
PP15,435 P2 12/2004 Sjulin et al.
PP15,596 P2 3/2005 Amorao et al.
PP15,731 P2 4/2005 Amorao et al.
PP15,752 P2 5/2005 Gilford et al.
PP16,070 P2 10/2005 Gilford et al.
PP16,238 P2 2/2006 Amorao et al.
PP16,241 P2 2/2006 Mowrey et al.
PP16,298 P2 2/2006 Gilford et al.
PP16,299 P2 2/2006 Gilford et al.
PP16,475 P2 4/2006 Gilford et al.
PP16,558 P3 5/2006 López
PP18,000 P2 9/2007 Meulenbroek
PP18,040 P3 9/2007 Mowrey et al.
PP18,041 P3 9/2007 Gilford
PP18,458 P2 1/2008 Ferguson et al.
PP18,575 P3 3/2008 Amorao et al.
PP18,878 P2 6/2008 Mowrey et al.
PP19,240 P2 9/2008 Gilford et al.
PP19,673 P3 2/2009 Ferguson et al.
PP19,767 P2 2/2009 Shaw et al.
PP20,248 P3 9/2009 Rogers et al.
PP20,363 P2 9/2009 Chandler
PP20,701 P2 2/2010 Gilford et al.
PP20,731 P2 2/2010 Mowrey et al.
PP20,733 P2 2/2010 Mowrey et al.

(Continued)

OTHER PUBLICATIONS

Ferguson et al, Unpublished U.S. Appl. No. 15/731,546, filed Jun. 26, 2017, titled "Strawberry Plant Variety Named 'DrisStrawFiftySix'".
Kibbe et al., Unpublished U.S. Appl. No. 15/731,542, filed Jun. 26, 2017, titled "Strawberry Plant Variety named 'DrisStrawFiftyTwo'".
Kibbe et al., Unpublished U.S. Appl. No. 15/731,545, filed Jun. 26, 2017, titled "Strawberry Plant Variety Named 'DrisStrawFiftyOne'".

(Continued)

*Primary Examiner* — Kent L Bell
(74) *Attorney, Agent, or Firm* — Morrison & Foerster LLP

(57) ABSTRACT

A new and distinct variety of strawberry plant named 'DrisStrawFiftyEight', particularly characterized by its yield potential, fruit size, conical fruit shape, shelf-life, and flavor and eating quality of fruit, is disclosed.

4 Drawing Sheets

(56) References Cited

U.S. PATENT DOCUMENTS

| | | | |
|---|---|---|---|
| PP20,735 | P2 | 2/2010 | Ferguson |
| PP20,775 | P2 | 2/2010 | Mowrey et al. |
| PP20,922 | P2 | 4/2010 | Gilford et al. |
| PP21,538 | P2 | 11/2010 | Gilford et al. |
| PP21,559 | P2 | 12/2010 | Ferguson et al. |
| PP21,762 | P2 | 3/2011 | Stewart et al. |
| PP22,040 | P3 | 7/2011 | Stewart et al. |
| PP22,218 | P2 | 11/2011 | Ferguson |
| PP22,247 | P2 | 11/2011 | Ferguson |
| PP23,107 | P2 | 10/2012 | Ferguson et al. |
| PP23,148 | P2 | 10/2012 | Gilford et al. |
| PP23,377 | P2 | 2/2013 | Ferguson et al. |
| PP23,378 | P2 | 2/2013 | Pullen et al. |
| PP23,382 | P2 | 2/2013 | Ferguson et al. |
| PP23,383 | P2 | 2/2013 | Ferguson et al. |
| PP23,400 | P2 | 2/2013 | Ferguson et al. |
| PP23,401 | P2 | 2/2013 | Pullen et al. |
| PP23,459 | P2 | 3/2013 | Stewart et al. |
| PP23,506 | P3 | 4/2013 | Ferguson et al. |
| PP23,517 | P3 | 4/2013 | Ferguson et al. |
| PP24,096 | P3 | 12/2013 | Fear et al. |
| PP24,317 | P3 | 3/2014 | Ferguson et al. |
| PP24,333 | P3 | 3/2014 | Vitten et al. |
| PP24,395 | P3 | 4/2014 | Vitten et al. |
| PP24,533 | P3 | 6/2014 | Ferguson et al. |
| PP24,745 | P2 | 8/2014 | Vitten et al. |
| PP25,408 | P3 | 4/2015 | Vitten et al. |
| PP25,437 | P3 | 4/2015 | Vitten et al. |
| PP25,698 | P3 | 7/2015 | Ferguson et al. |
| PP25,699 | P3 | 7/2015 | Stewart et al. |
| PP25,747 | P3 | 7/2015 | Kibbe et al. |
| PP25,866 | P3 | 9/2015 | Ferguson et al. |
| PP26,800 | P3 | 6/2016 | Stewart et al. |
| PP26,801 | P3 | 6/2016 | Stewart et al. |
| PP26,802 | P3 | 6/2016 | Rodriguez Alcazar et al. |
| PP27,442 | P2 | 12/2016 | Kibbe et al. |
| PP27,645 | P3 | 2/2017 | Vitten et al. |
| PP27,682 | P3 | 2/2017 | Kibbe et al. |
| PP27,711 | P3 | 2/2017 | Vitten et al. |
| PP27,813 | P3 | 3/2017 | Ferguson et al. |
| PP29,289 | P3 | 5/2018 | Vitten et al. |
| 2003/0079263 | P1 | 4/2003 | Gilford et al. |
| 2013/0276182 | P1 | 10/2013 | Fear et al. |

OTHER PUBLICATIONS

Mendoza et al., Unpublished U.S. Appl. No. 15/998,020, filed Jun. 12, 2018, titled "Strawberry Plant Variety named 'DrisStrawSixtyOne'".

Pakozdi et al., Unpublished U.S. Appl. No. 15/998,015, filed Jun. 11, 2018, titled "Strawberry Plant Variety Named 'DrisStrawFiftyNine'".

Pakozdi et al., Unpublished U.S. Appl. No. 15/998,028, filed Jun. 14, 2018, titled "Strawberry Plant Variety Named 'DrisStrawSixtyFive'".

Stewart et al., Unpublished U.S. Appl. No. 15/731,415, filed Jun. 6, 2017, titled "Strawberry Plant Variety Named 'DrisStrawFiftyThree'".

Stewart et al., Unpublished U.S. Appl. No. 15/731,421, filed Jun. 6, 2017, titled "Strawberry Plant Variety Named 'DrisStrawFiftySeven'".

Stewart et al., Unpublished U.S. Appl. No. 15/998,031, filed Jun. 14, 2018, titled "Strawberry Plant Variety Named 'DrisStrawSixtyFour'".

Vitten et al., Unpublished U.S. Appl. No. 15/731,559, filed Jun. 27, 2017, titled "Strawberry Plant Variety Named 'DrisStrawFiftyFour'".

Vitten et al., Unpublished U.S. Appl. No. 15/731,560, filed Jun. 27, 2017, titled "Strawberry Plant Variety Named 'DrisStrawFiftyFive'".

"An Early Season With Many Highs", Berry Gardens, Available Online at <https://www.berrygardens.co.uk/an-early-season-with-many-highs/>, Aug. 21, 2017, 6 pages.

Katie, "My Green Pod", Available online at <https://www.mygreenpod.com/articles/its-strawberry-time/>, May 30, 2017, 3 pages.

STRAWBERRY PLANT VARIETY NAMED 'DRISSTRAWFIFTYEIGHT'

Latin name: Botanical classification: *Fragaria* x *ananassa*.

Varietal denomination: The varietal denomination of the claimed variety of strawberry plant is 'DrisStrawFiftyEight'.

BACKGROUND OF THE INVENTION

Cultivated strawberry is a hybrid species of the genus *Fragaria* that is grown worldwide for its fruit. Modern strawberry was first bred in Brittany, France, in the 18$^{th}$ century by crossing *Fragaria virginiana* with *Fragaria chiloensis*. Strawberry fruit is an aggregate accessory fruit, with the fleshy part of the fruit being derived from the receptacle that holds the ovaries.

Strawberry varieties vary widely in color, size, shape, flavor, season of ripening, degree of fertility, and susceptibility to disease. Certain varieties vary in foliage, and some vary in the relative development of their reproductive organs. Typically, strawberry flowers appear hermaphroditic in structure, but function as either male or female. Generally, commercial production of strawberry plants involves propagation from runners and distribution as either plugs or bare root plants. Cultivation is either perennial or annual plasticulture. During the off season, strawberries can also be produced in greenhouses.

Strawberry fruit is widely appreciated for its characteristic bright red color, aroma, juicy texture, and sweetness. Strawberry fruit is a popular fruit that is generally consumed either fresh or in prepared foods, such as preserves and baked goods.

Strawberry is an important and valuable fruit crop. Accordingly, there is a need for new varieties of strawberry plants. In particular, there is a need for improved varieties of strawberry plant that are stable, high yielding, and agronomically sound.

SUMMARY OF THE INVENTION

In order to meet these needs, the present invention is directed to an improved variety of strawberry plant. In particular, the invention relates to a new and distinct variety of strawberry plant (*Fragaria* x *ananassa*), which has been denominated as 'DrisStrawFiftyEight'.

Strawberry plant variety 'DrisStrawFiftyEight' was discovered in Kent County, the United Kingdom in July of 2011, and originated from a cross between the proprietary female parent 'TUKE 278-050' (unpatented) and the proprietary male parent 'SUKE 103-064' (unpatented). A single plant was selected and asexually propagated via stolons in the Netherlands in July of 2011.

'DrisStrawFiftyEight' was subsequently asexually propagated via stolons, and underwent further testing at a farm in Kent County, the United Kingdom for six years (2011 to 2016). The present variety has been found to be stable and reproduce true to type through successive asexual propagations via stolons.

'DrisStrawFiftyEight' exhibits the following distinguishing characteristics when grown under normal horticultural practices in Kent County, the United Kingdom:

1. Significantly high yield; and
2. Large fruit size.

'DrisStrawFiftyEight' was selected for its yield potential, fruit size, conical fruit shape, shelf-life, and flavor and eating quality of fruit.

DESCRIPTION OF THE DRAWINGS

This new strawberry plant is illustrated by the accompanying photographs which show fruit, flowers, and leaves of the plant. The colors shown are as true as can be reasonably obtained by conventional photographic procedures. The photographs are of plants that are three months old.

DESCRIPTION OF THE NEW VARIETY

Figure 1:
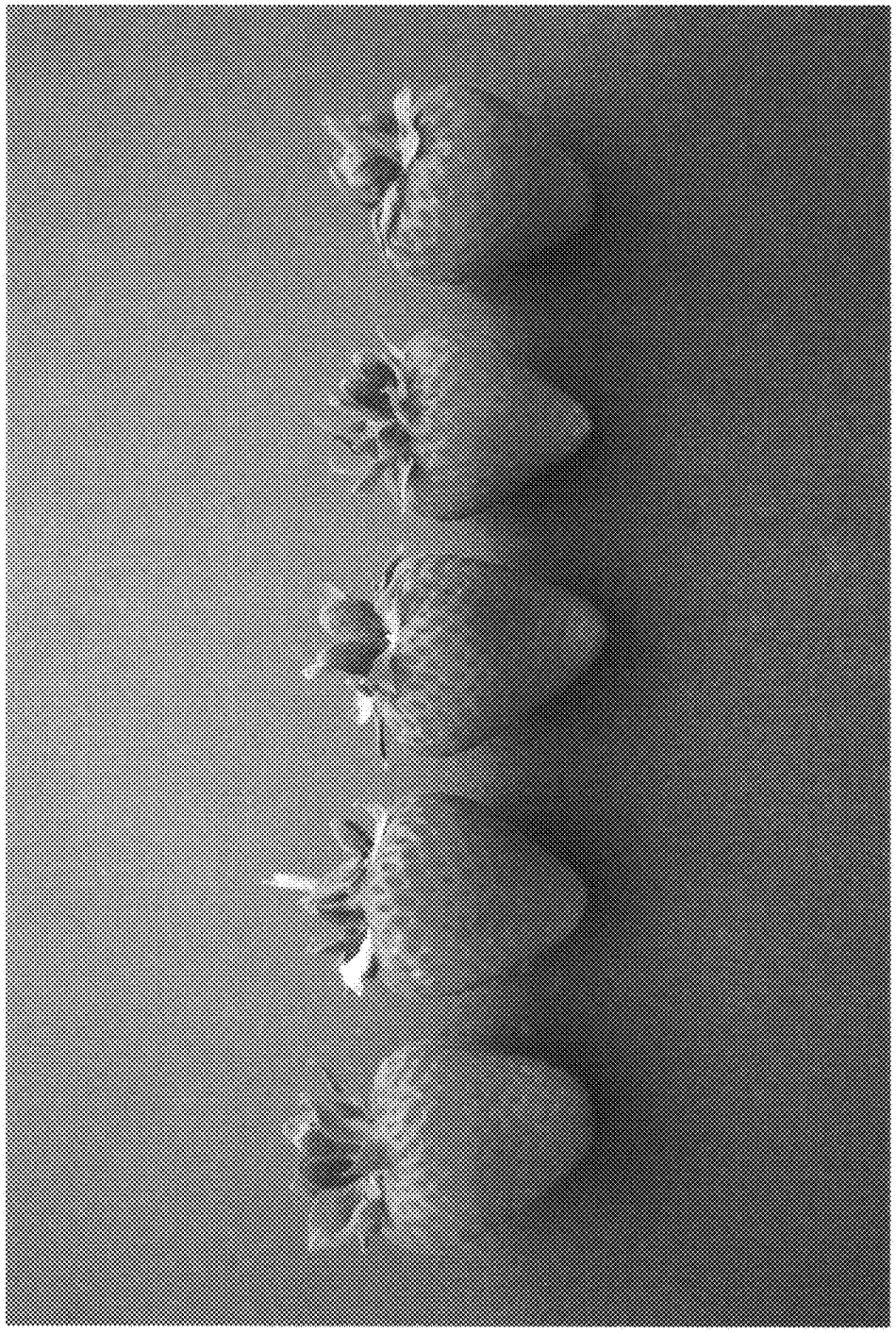
FIG. 1 illustrates whole fruit of variety 'DrisStrawFiftyEight'.
Figure 2:
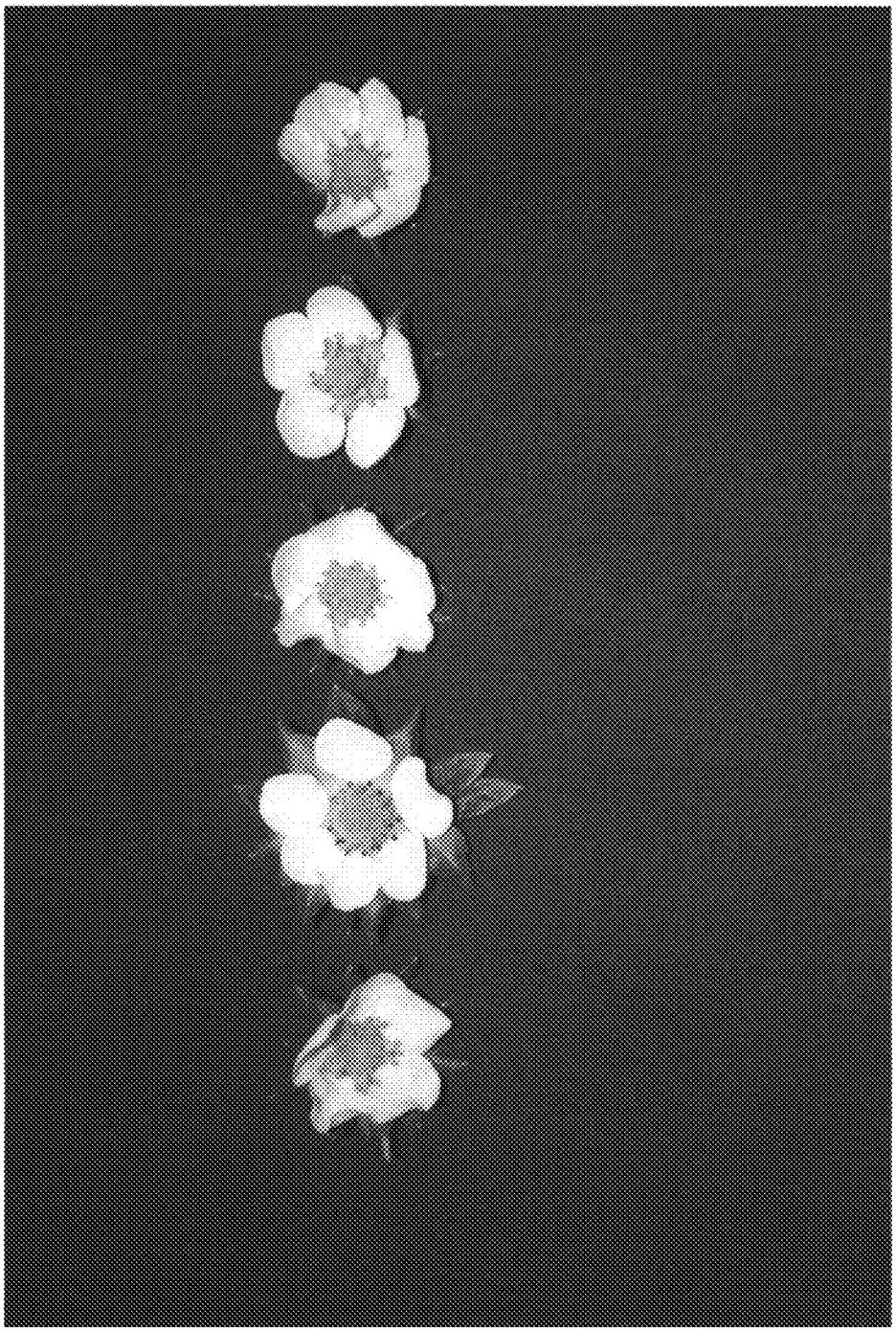
FIG. 2 illustrates the upper surface of flowers of variety 'DrisStrawFiftyEight'.
Figure 3:
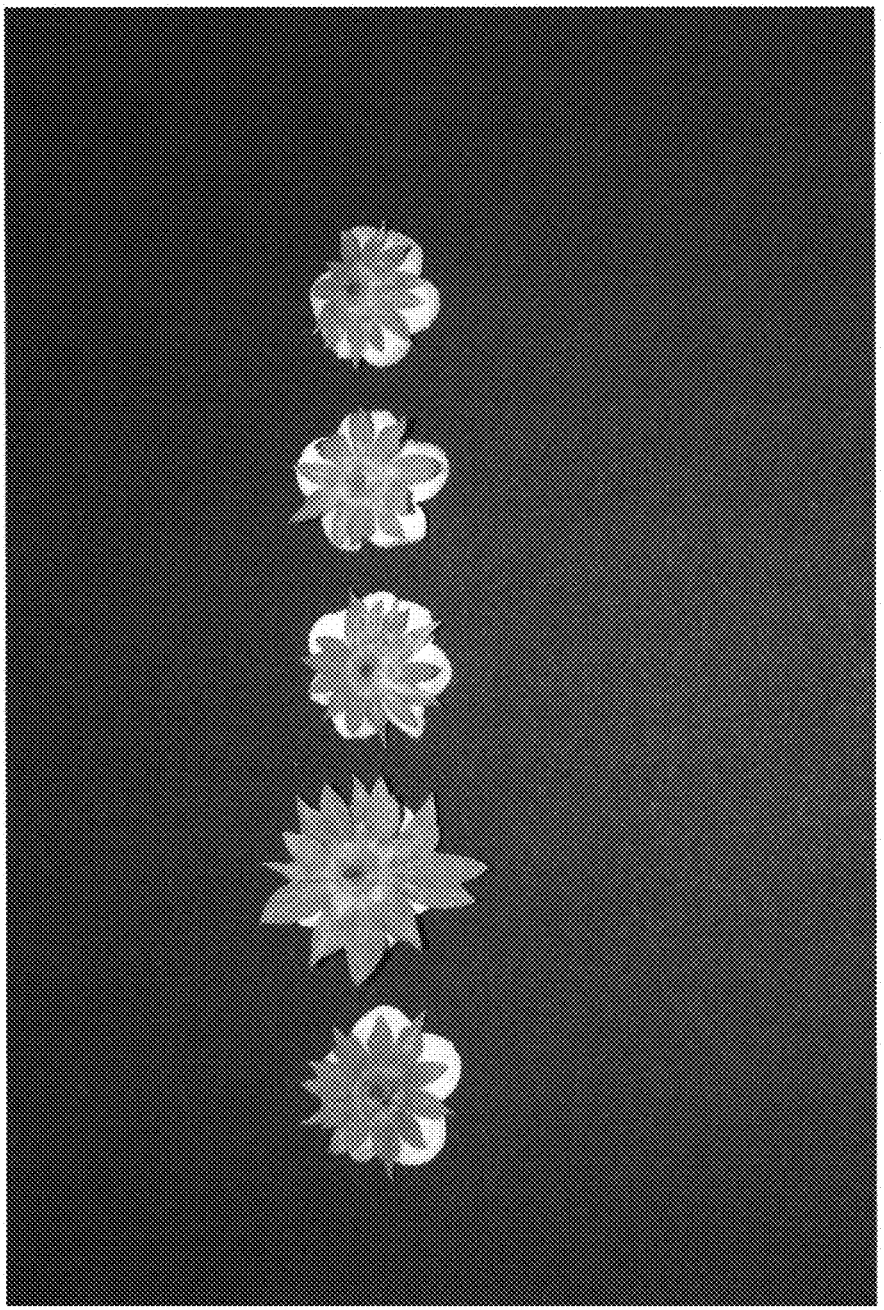
FIG. 3 illustrates the lower surface of flowers of variety 'DrisStrawFiftyEight'.
Figures 4A, 4B:
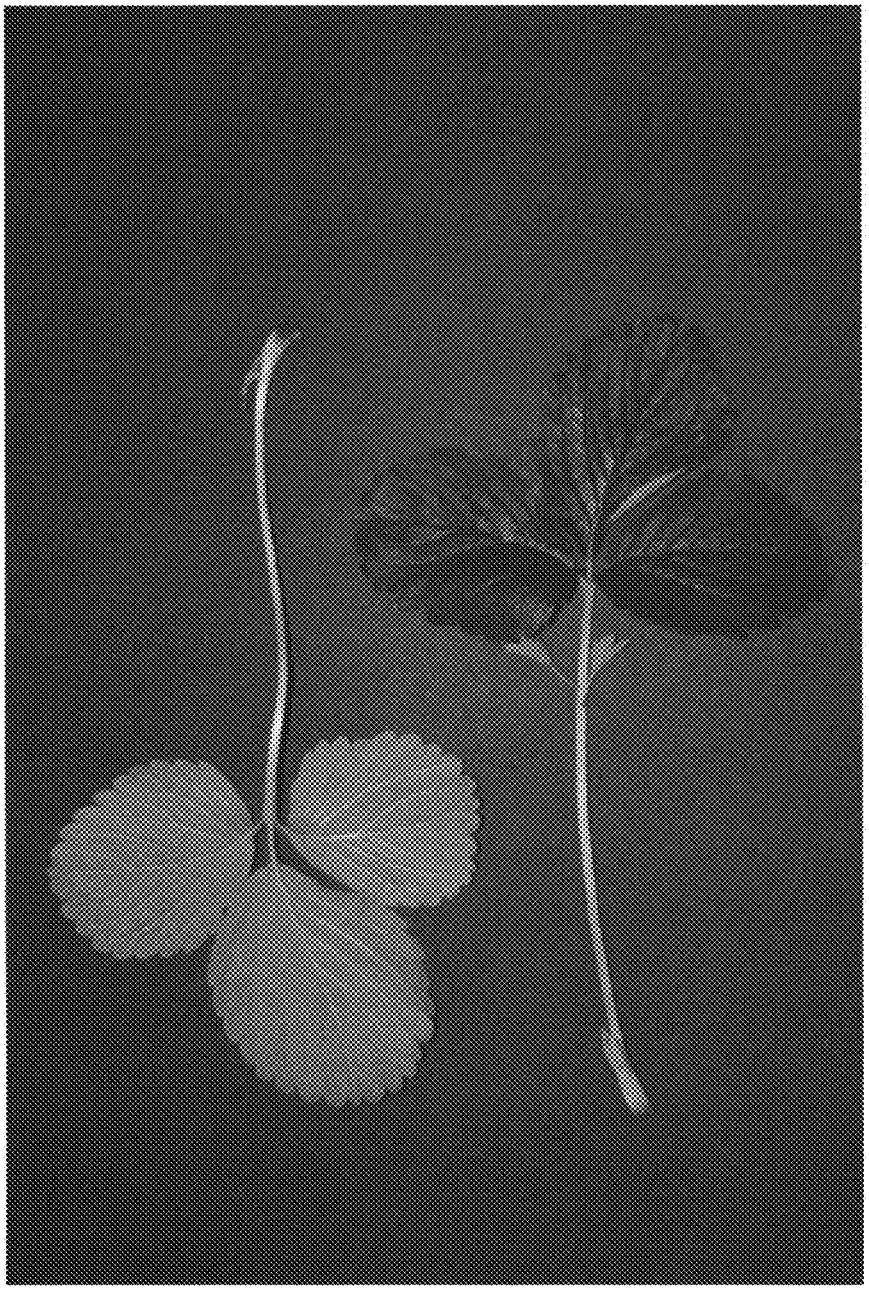
FIG. 4A illustrates the lower surface of a leaf of variety 'DrisStrawFiftyEight'.
FIG. 4B illustrates the upper surface of a leaf of variety 'DrisStrawFiftyEight'.

The following detailed descriptions set forth the distinctive characteristics of 'DrisStrawFiftyEight'. The data which define these characteristics is based on observations taken in Kent County, the United Kingdom from 2011 to 2016. This description is in accordance with UPOV terminology. Color designations, color descriptions, and other phenotypical descriptions may deviate from the stated values and descriptions depending upon variation in environmental, seasonal, climatic, and cultural conditions. 'DrisStrawFiftyEight' has not been observed under all possible environmental conditions. The botanical description of 'DrisStrawFiftyEight' was taken from plants that were three months old. The indicated values represent averages calculated from measurements of several plants. Color references are primarily to The R.H.S. Colour Chart of The Royal Horticultural Society of London (R.H.S.) (2007 edition). Descriptive terminology follows the *Plant Identification Terminology, An Illustrated Glossary,* 2$^{nd}$ edition by James G. Harris and Melinda Woolf Harris, unless where otherwise defined.

DETAILED BOTANICAL DESCRIPTION OF THE PLANT

Classification:

*Species.*—*Fragaria* x *ananassa.*

*Common name.*—Strawberry.

*Denomination.*—'DrisStrawFiftyEight'.

Parentage:

*Female parent.*—The proprietary variety 'TUKE 278-050' (unpatented).

*Male parent.*—The proprietary variety 'SUKE 103-064' (unpatented).

Plant:

*Height.*—39.5 cm.

*Diameter.*—39.5 cm.

*Number of crowns/plant.*—4.

*Growth habit.*—Upright.

Stolon:

*Average number of daughter plants per square foot.*—36-45.

*Diameter at bract.*—3.113 mm.

*Anthocyanin coloration.*—Present.

*Anthocyanin color.*—RHS 63B (Strong purplish red).

Leaf:

*Number of leaflets.*—Sometimes more than three.

*Color of upper surface.*—RHS 137A (Moderate olive green).

*Color of lower surface*.—RHS 137C (Moderate yellow green).

*Variegation*.—Absent.

*Terminal leaflets*.—Length: 9.0 cm. Width: 8.5 cm. Length/width ratio: 1.1. Number of teeth/terminal leaflet: 19. Leaflet shape: Flat straight. Shape of apex: Rounded. Shape of base: Acute. Margin: Serrate to crenate. Shape in cross section: Concave.

*Petiole*.—Length: 29.9 cm. Diameter: 5.98 mm. Color: RHS 144B (Strong yellow green). Attitude of hairs: Horizontal. Bract frequency (number present on each petiole): 1.

*Petiolule*.—Length: 8.60 mm. Diameter: 2.10 mm. Color: RHS 144C (Strong yellow green).

*Stipule*.—Length: 3.3 cm. Width: 10.82 mm. Anthocyanin coloration: Present. Anthocyanin color: RHS 65A (Moderate purplish pink).

Inflorescence:

*Position in relation to foliage*.—Above.

*Pedicel*.—Length: 66.00 mm. Diameter: 1.62 mm. Color: RHS 144C (Strong yellow green). Attitude of hairs: Upwards.

*Flower*.—Flower diameter (petal tip to petal tip on non-flattened flower): 30.74 mm. Flower depth: 9.51 mm. Arrangement of petals: Overlapping. Stamen: Present. Typical and observed number of flowers per plant: 33.

*Petal*.—Length: 12.62 mm. Width: 12.59 mm. Length/width ratio: 1.0. Petal shape: Obicular. Shape of apex: Rounded. Shape of base: Rounded. Margin: Entire. Typical and observed petal number: 6. Color of upper side: RHS NN155C (White). Color of lower side: RHS NN155C (White).

*Calyx*.—Diameter (sepal tip to sepal tip, measured on back of flower): 32.73 mm.

*Sepal*.—Length (sepal tip to point of attachment to receptacle): 16.77 mm. Width: 6.84 mm. Color of upper surface: RHS 141B (Deep yellowish green). Color of lower surface: RHS 143A (Strong yellow green). Sepal shape: Elliptical. Shape of apex: Truncate. Margin: Entire. Typical and observed sepal number: 6.

Fruit:

*Length*.—46.36 mm.

*Width*.—38.96 mm.

*Weight* (*individual fruit*).—19.0 g.

*Length/width ratio*.—1.2.

*Fruit hollow length*.—38.97 mm.

*Fruit hollow width*.—24.33 mm.

*Fruit hollow length/width ratio*.—1.6.

*Shape*.—Conical.

*Color*.—RHS 44A (Vivid red).

*Position of achenes*.—Below surface.

*Color of achenes*.—RHS N144B (Strong yellow).

*Position of calyx attachment*.—Level with fruit.

*Attitude of sepals*.—Outwards.

*Color of flesh* (*excluding core*).—RHS 44B (Vivid reddish orange).

*Color of core*.—RHS 44C (Vivid reddish orange).

*Fruiting truss*.—Length: 33.20 cm. Diameter: 5.69 cm. Color: RHS 144B (Strong yellow green). Number of berries per truss: 12 berries.

Production:

*Flowering interval*.—June to September.

*Harvest interval*.—July to September.

*Type of bearing*.—Fully remontant.

*Productivity*.—1.306 kg to 1.400 kg of fruit per season from two-month-old to six-month-old plants when grown in Kent County, the United Kingdom.

Resistance to diseases:

*Powdery mildew* (*podosphaera macularis*).—Moderately resistant.

*Verticillium wilt*.—Moderately susceptible.

COMPARISON WITH PARENTAL AND COMMERCIAL VARIETIES

'DrisStrawFiftyEight' differs from the proprietary female parent 'TUKE 278-050' (unpatented) in that plants of 'DrisStrawFiftyEight' produce higher yields of fruit as compared to plants of 'TUKE 278-050'. Additionally, fruit of 'DrisStrawFiftyEight' are larger in size and have a lighter red color as compared to fruit of 'TUKE 278-050'.

'DrisStrawFiftyEight' differs from the proprietary male parent 'SUKE 103-064' (unpatented) in that plants of 'DrisStrawFiftyEight' produce higher yields of fruit as compared to plants of 'SUKE 103-064'. Additionally, fruit of 'DrisStrawFiftyEight' are larger in size as compared to fruit of 'SUKE 103-064'.

'DrisStrawFiftyEight' differs from the commercial variety 'DrisStrawTwo' (U.S. Plant Pat. No. 18,878) in that plants of 'DrisStrawFiftyEight' have an upright growth habit, while plants of 'DrisStrawTwo' have a semi-upright growth habit. Additionally, fruit of 'DrisStrawFiftyEight' have absent or a very narrow width of band without achenes, while fruit of 'DrisStrawTwo' have a medium width of band without achenes. Moreover, fruit of 'DrisStrawFiftyEight' have a calyx attachment that is level with fruit, while fruit of 'DrisStrawTwo' have a calyx attachment that is raised from fruit.

'DrisStrawFiftyEight' differs from the commercial variety 'DrisStrawThirtyEight' (U.S. Plant Pat. No. 25,437) in that plants of 'DrisStrawFiftyEight' have an upright growth habit, while plants of 'DrisStrawThirtyEight' have a semi-upright growth habit. Additionally, fruit of 'DrisStrawFiftyEight' are large in size, while fruit of 'DrisStrawThirtyEight' are medium in size. Moreover, fruit of 'DrisStrawFiftyEight' have achenes that are below surface of fruit, while fruit of 'DrisStrawTwo' have achenes that are level with or above surface of fruit.

We claim:

1. A new and distinct variety of strawberry plant named 'DrisStrawFiftyEight' as shown and described herein.

* * * * *